(12) United States Patent
Cochran et al.

(10) Patent No.: US 6,936,740 B1
(45) Date of Patent: Aug. 30, 2005

(54) DENSE PHASE OXIDATION OF BENZENE

(75) Inventors: Robert N. Cochran, West Chester, PA (US); Jay F. Miller, Chester Springs, PA (US); Eric John Beckman, Aspinwall, PA (US); Sarah Emma Jones, Flintshire (GB)

(73) Assignee: ARCO Chemical Technology, L.P., Greenville, DE (US)

( * ) Notice: Subject to any disclaimer, the term of this patent is extended or adjusted under 35 U.S.C. 154(b) by 36 days.

(21) Appl. No.: 10/921,686

(22) Filed: Aug. 19, 2004

(51) Int. Cl.$^7$ ............................................. L07L 37/00
(52) U.S. Cl. ...................................... 568/802; 568/800
(58) Field of Search ................................ 568/800, 802

(56) References Cited

U.S. PATENT DOCUMENTS

| | | |
|---|---|---|
| 4,408,081 A | 10/1983 | Foster |
| 4,408,082 A | 10/1983 | Baumgartner |
| 5,110,995 A | 5/1992 | Kharitonov et al. |
| 5,744,619 A | 4/1998 | Nemeth et al. |
| 5,780,654 A | 7/1998 | Nemeth et al. |
| 6,710,192 B2 | 3/2004 | Hancu et al. |

*Primary Examiner*—Michael L. Shippen
(74) *Attorney, Agent, or Firm*—William C. Long

(57) ABSTRACT

Phenol is formed by reaction of oxidant and benzene over a solid catalyst such as Pd on TS-1, the reaction being carried out in carbon dioxide solvent at conditions effective to provide a dense phase reaction mixture.

8 Claims, No Drawings

DENSE PHASE OXIDATION OF BENZENE

FIELD OF THE INVENTION

The present invention relates to the oxidation of benzene to phenol using a solid catalyst such as Pd on TS-1, the improvement being that the reaction is carried out in carbon dioxide solvent under dense reaction mixture phase conditions.

BACKGROUND OF THE INVENTION

Phenol is an important chemical of commerce. Many different methods for synthesizing phenol have been described in the literature, most notably the phenol/acetone remote from cumene. In addition, it has been proposed to produce phenol by oxidation of benzene; see, e.g. U.S. Pat. No. 5,110,995 wherein nitrous oxide is employed as oxidant in the reaction.

As with any process to produce a commercial chemical, it would be desirable to attain further improvements in phenol production.

Dense phase reaction mixture conditions have been employed in various reaction systems, e.g. in the production of tertiary butyl hydroperoxide by direct oxidation of isobutene. See, for example, U.S. Pat. Nos. 4,408,081 and 4,408,082. See also U.S. Pat. No. 6,710,192 wherein propylene oxide is formed by epoxidation of propylene under dense phase reaction conditions.

SUMMARY OF THE INVENTION

In accordance with the present invention, the oxidation of benzene to produce phenol is carried out by reacting benzene and oxidant, using an appropriate catalyst, the reaction being carried out using $CO_2$ as the essential solvent at dense phase reaction conditions.

DETAILED DESCRIPTION

There are a number of significant advantages which are achieved through practice of the present invention. $CO_2$ is the essential solvent used for the reaction and by products, which are generally formed in systems using organic solvents, are substantially avoided. Where a noble metal supported catalyst is used, leaching of noble metal from the solid catalyst is minimal due to insolubility in $CO_2$. Because the benzene and oxidants are totally miscible in the dense phase system, better control of the reagent concentrations can be achieved and the head space in the reactor can be substantially eliminated.

The catalysts to be used in the present process preferably are comprised of a titanium or vanadium zeolite and a noble metal (preferably an element of Group VIII of the Periodic Table). Suitable zeolites are those crystalline materials having a porous molecular sieve structure with titanium or vanadium atoms substituted in the framework. The use of a TS-1 titanium silicalite or vanadium silicalite is especially advantageous.

The titanium-containing zeolites useful as catalysts in the process comprise the class of zeolitic substances wherein titanium atoms are substituted for a portion of the silicon atoms in the lattice framework of a molecular sieve. Such substances are well known in the art.

Particularly preferred titanium-containing zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta, mordenite, ZSM-48, ZSM-12, and MCM-41. The titanium-containing zeolite preferably contains no elements other than titanium, silicon and oxygen in the lattice framework, although minor amounts of boron, iron, aluminum, and the like may be present. Other metals such as tin or vanadium may also be present in the lattice framework of the zeolite in addition to the titanium, as described in U.S. Pat. Nos. 5,780,654 and 5,744,619.

Preferred titanium-containing zeolite catalysts suitable for use in the process of this invention will generally have a composition corresponding to the following empirical formula $xTiO_2 (1-x)SiO_2$ where x is between 0.0001 and 0.500. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 20 weight percent, preferably 0.1 to 5 weight percent. The manner in which the noble metal is incorporated into the catalyst is not considered to be particularly critical. For example, the noble metal may be supported on the zeolite by impregnation means or the like or first supported on another substance such as silica, alumina, activated carbon or the like and then physically mixed with the zeolite. Alternatively, the noble metal can be incorporated into the zeolite by ion-exchange with, for example, Pd tetraammine chloride with or without added ammonium hydroxide. The catalyst is recovered by filtration and washing and is substantially free (0.1 wt. % or less) of halide. There are no particular restrictions regarding the choice of noble metal compound or complex used as the source of the noble metal. For example, suitable compounds for such purpose include the nitrates, sulfates, halides (e.g., chlorides, bromides), carboxylates (e.g., acetate), and amine complexes of noble metals. Similarly, the oxidation state of the noble metal is not considered critical. In the case of palladium for instance, the palladium may be in an oxidation state anywhere from 0 to +4 or any combination of such oxidation states. To achieve the desired oxidation state or combination of oxidation states, the noble metal compound after being introduced into the catalyst may be fully or partially pre-reduced. Satisfactory catalytic performance can, however, be attained without any pre-reduction whatsoever. To achieve the active state of palladium, the catalyst may undergo pretreatment such as thermal treatment in nitrogen, vacuum, hydrogen or air.

The catalyst may additionally comprise a binder or the like and may be molded, spray dried, shaped or extruded into any desired form prior to use in epoxidation. In addition to the noble metal, the catalyst may be modified with additional elements such as, for example, lanthanide metals. (e.g., europium), iron, cobalt, nickel, boron, aluminum, phosphorus, calcium, vanadium, chromium, manganese, copper, zinc, and gallium.

Alternatively, others of the various catalysts known for use in the oxidation of benzene to phenol can also be used. For example, U.S. Pat. No. 5,110,995 describes reacting nitrous oxide with benzene to form phenol using various zeolitic catalysts such as iron silicate with ZSM-5 structure. The reaction systems and catalysts described in U.S. Pat. No. 5,110,995 can be employed in practice of the present invention, the disclosure of U.S. Pat. No. 5,110,995 is incorporated herein by reference.

Nitrous oxide is a suitable oxidant when used with catalysts described in U.S. Pat. No. 5,110,995. Where noble metal on titanium silicate is used, the reactant gases comprise mixtures of oxygen and hydrogen as hereinafter described.

The oxidation reaction is carried out using $CO_2$ as essential solvent, at conditions which are effective to provide a single dense phase reaction mixture. Although small amounts of other solvents can be tolerated, it is preferred that $CO_2$ comprise the major amount and preferably at least 98% by weight of the reaction solvent. The $CO_2$ solvent comprises at least about 10 wt % of the reaction mixture, preferably about 75% or more up to 95% or more.

A dense-phase feed reaction mixture is one maintained at a pressure sufficiently elevated so that the reaction mixture comprised of benzene —$CO_2$-oxidant behaves like a single, dense, liquid-like phase with a density higher than 0.25 g/cm$^3$. Suitable temperatures are in the range of 20 to 100° C. and suitable pressures from 10 to 300 atm. In other words, the dense-phase reaction mixture is free of the vapor phase, which has been characteristic of prior art reactions in the vapor phase or in a two phase (vapor-liquid) mixture. Preferably, the feed reaction mixture is under supercritical conditions, that is, a mixture comprising of oxidant and $CO_2$ is maintained above its critical temperature as well as above its critical pressure. The oxygen and hydrogen or nitrous oxide are present in solution in the dense phase mixture, not as a separate vapor phase.

Although the critical points of temperature and pressure of $CO_2$ of 31.1° C. and 72.9 atm are useful in establishing conditions for carrying out the reaction in accordance with the invention, suitable operating conditions are pressure of 15 to 300 atm and temperatures of 20 to 100° C. Where the oxidant comprises oxygen/hydrogen mixtures, the molar ratio of hydrogen to oxygen can usually be varied in the range of $H_2:O_2$=1:10 to 5:1 and is especially favorable at 1:5 to 2:1. The molar ratio of oxygen or nitrous oxide to benzene is usually 1:1 to 1:20, and preferably 1:1.5 to 1:10.

The following examples illustrate practice of the invention.

EXAMPLE 1

The reaction was carried out in a stainless steel batch reactor (volume 42 cm$^3$) connected to three high pressure syringe pumps (High Pressure Equipment, 30 cm$^3$), a high pressure recirculating pump (Micropump) and a Hewlett Packard 5890 Series 2 Gas Chromatograph with both TCD and FID detectors. The reactor was charged with Pd/TS-1 catalyst (0.153 g), 0.34 wt % Pd, and benzene (5.6 mmol) and the system was then evacuated under vacuum. The reactor was heated to 70° C. and known amounts of hydrogen (2.5 mmol), $CO_2$ (32.8 mmol) and oxygen (5.9 mmol-from air) were added (in this order). Additional $CO_2$ (AGA Speciality Gas, Coleman grade, 99.99%, approximately 20 g) was added via a gas booster (single stage, Haskel) to reach 2200 psi, to provide a dense phase reaction mixture. The reaction mixture was stirred vigorously throughout the reaction. The dense phase was analyzed at various time intervals by on-line GC and then slowly depressurized to atmospheric pressure. Over a two hour period, phenol was produced at the rate of 0.0276 g/g catalyst—hour.

EXAMPLE 2

Benzene (5.6 mmol), hydrogen (2.5 mmol) and oxygen 5.9 mmol-from air) were added into the reactor to form phenol as described in Example 1. 0.075 g of the same Pd/TS-1 catalyst as used in Example 1 was added into the reactor. Approximately 20 g of $CO_2$ was added as the solvent and the reaction was carried out in the dense phase at 70° C. and 2200 psi. Over a two hour period, phenol was produced at the rate of 0.7 g/g catalyst—hour.

EXAMPLE 3

Benzene (5.6 mmol), hydrogen (2.5 mmol) and oxygen (5.9 mmol-from air) were added into the reactor to form phenol as described in Example 1. 0.041 g of the same Pd/TS-1 catalyst used above was added into the reactor. Approximately 20 g of $CO_2$ was added as the solvent and the reaction was carried out in the dense phase at 70° C. and 2200 psi. Over a two hour period, phenol was produced at the rate of 0.73 g/g catalyst—hour.

EXAMPLES 4–9

Using the equipment and catalyst described above in Example 1, a series of runs were made with the amount of catalyst and the reaction time being varied. The reactor was charged with the indicated amount of Pd/TS-1 catalyst and 11 m mol benzene. The system was evacuated under vacuum. The system was heated to 60° C. and 5 m mols of hydrogen and 10 m mols of oxygen were added. $CO_2$ was added to pressurize the system to 2700 psi and the reaction was conducted for the designated times. The results obtained are shown in Table 1.

TABLE 1

| Example | Catalyst Weight (mg) | Time (hours) | Phenol yield (moles phenol/ moles benzene) × 100 |
|---|---|---|---|
| 4 | 300 | 4 | 0.11 |
| 5 | 300 | 2 | 0.032 |
| 6 | 300 | 3 | 0.042 |
| 7 | 75 | 4 | 0.0025 |
| 8 | 300 | 4 | 0.0708 |
| 9 | 150 | 4 | 0.0043 |

A GC trace showed there were no products other than phenol formed.

The above examples demonstrate the highly selective production of phenol achieved through practice of the invention. Analysis of the reaction products in each case showed only phenol as product; no substantial amounts of other reaction products were detected.

We claim:

1. In a process for the production of phenol by contacting oxidant and benzene at reactive conditions with a solid catalyst, the improvement which comprises carrying out the reaction in carbon dioxide solvent at conditions effective to provide a dense phase reaction mixture.

2. The process of claim 1 wherein the catalyst is noble metal on titanium or vanadium silicalite.

3. The process of claim 1 wherein the catalyst is Pd on TS-1.

4. The process of claim 1 wherein the reaction is carried out at is a temperature of 20 to 100° C. and a pressure of 10–300 atm.

5. The process of claim 1 wherein the oxidant comprises a mixture of oxygen and hydrogen.

6. The process of claim 1 wherein the oxidant comprises nitrous oxide.

7. The process of claim 5 wherein the molar ratio of hydrogen to oxygen in the oxidant is in the range 1:10 to 5:1.

8. The process of claim 1 wherein the molar ratio of oxidant to benzene is in the range 1:1 to 1:20.

* * * * *